United States Patent
Namimatsu

(10) Patent No.: US 6,960,450 B2
(45) Date of Patent: Nov. 1, 2005

(54) ANTIGEN ACTIVATING METHOD AND ANTIGEN ACTIVATOR

(76) Inventor: Shigeki Namimatsu, Arusu Kawagoe Rm. 106, 3-9-4, Shinjuku-cho, Kawagoe-shi, Saitama-ken (JP)

(*) Notice: Subject to any disclaimer, the term of this patent is extended or adjusted under 35 U.S.C. 154(b) by 616 days.

(21) Appl. No.: 10/092,462

(22) Filed: Mar. 8, 2002

(65) Prior Publication Data

US 2002/0182653 A1 Dec. 5, 2002

(30) Foreign Application Priority Data

May 29, 2001 (JP) .................................. 2001-160424

(51) Int. Cl.[7] .......................... G01N 1/30; G01N 33/48
(52) U.S. Cl. ................... 435/40.5; 435/40.52; 436/141; 436/129; 424/78.2
(58) Field of Search ....................... 435/40.52; 436/141; 436/129; 424/78.2

(56) References Cited

U.S. PATENT DOCUMENTS

| | | |
|---|---|---|
| 5,244,787 A | 9/1993 | Key et al. |
| 5,578,452 A | 11/1996 | Shi et al. |

OTHER PUBLICATIONS

Shigeki Namimatsu et al; Reversing the Effects of Formalin Fixation with Citraconic Anhydride and Heat : A Universal Antigen Retrieval Method; Mar. 11, 2005; vol. 53(1); pp. 1–11; Journal of Histochemistry & Cytochemistry.
Shi S.R., Key, M.E., Kalra, K.L.; Antigen retrieval in formalin–fixed paraffin–embedded tissues: an enhancement method for immunohistochemical staining based on microwave oven heating of tissue sections. J. Histochem. 39: 741–748, 1991.
Shi S.R., Cote R.J., Young L., Imam S.A. Taylor C.R.: Use of pH9.5 Tris–HCl buffer containing 5% urea for antigen retrieval immunohistochemistry, Biotechnic & Histochemistry 71(4): 190–6, 1996 Jul. 1996.
Cattoretti G., Becker M.H.G., Key G., et al.: Monoclonal antibodies produced against recombinant parts of the Ki–67 molecule (MIB–1 to–3) stain proliferating cells in formalin fixed, paraffin–embedded, microwave processed tissues. Histochem J. 234:611, 1992 (Abstr).
Shin R.W., Iwaki T., Kitamono T., et al.: Hydrated autoclave pretreatment enhances tau immunoreactivity in formalin–fixed normal and Alzheimer's disease brain tissues. Lab. Invest. 64: 693–702, 1991.
Hamakawa Shinji: An investigation on antigen activation by heat treatment during enzyme–antibody staining using anti–CD4 monoclonal antibody (Byohri to Rinshoh (Pathology and Clinical Pathology)) 1999, 17(11): 1201–1205).
Hamakawa Shinji: An investigation on an antigen activator in place of EDTA solution (Byohri Gijutu (Pathological Techniques)) 1999, 60:10–14.
Shan–Rong Shi et al., Antigen Retrieval Techniques: Current Prespectives, Journal of Histochemistry and Cytochemistry, vol. 49, 931–938, Aug. 2001, (13 pages).
Shan–Rong Shi et al., Antigen Retrieval Immunohistochemistry: Past, Present, and Future, Journal of Histochemistry and Cytochemistry, vol. 45, 327–344 (30 pages).

*Primary Examiner*—Long V. Le
*Assistant Examiner*—Deborah A. Davis
(74) *Attorney, Agent, or Firm*—Shlesinger Arkwright & Garvey LLP

(57) ABSTRACT

An object of the present invention is to provide a reagent for activating and unmasking antigens in a immuno-tissue-chemical staining. A slice of tissue cells on a slide glass is heated or heated under pressurization by an electric pot, autoclave, microwave oven, scalder, or constant-temperature bath for a sufficient time period in CCA aqueous solution of suitable pH and CCA concentration, thereby activating and unmasking antigenicity of antigen masked by aldehyde fixation.

9 Claims, 1 Drawing Sheet

ANTIGEN ACTIVATING METHOD AND ANTIGEN ACTIVATOR

BACKGROUND OF THE INVENTION

1. Technical Field of the Invention

The present invention relates to an antigen activator and a method for activating an antigen immuno-cell or immuno-tissue during chemical staining, and particularly to an improved method and a regent thereof for expose (activate, unmask, or retrieve) an antigenicity, when cells or tissues on a slide glass are stained immuno-tissue-chemically.

2. Description of the Prior Art

Conventionally three antigen activators such as citrate buffer solution, urea added tris salt buffer solution, and ethylenediaminetetraacetate (EDTA) are mainly used for activating the antigen during immuno-staining by heat and pressurization treatment.

Concretely, the following antigen activation methods are known;

(1) The activation method by using a citrate buffer solution of pH 6.0 and concentration 0.01 mol. and by pressurization, heating, or humidification by using a microwave oven, autoclave, electric pot, constant-temperature bath, or scalder.

(2) The activation method by using a citrate buffer solution of pH 7.0 and concentration 0.01 mol. containing 5% urea by pressurization and and heating by using an autoclave.

(3) The activation method by using pH 9.5 and concentration 0.1 mol. tris-HCl buffer solution containing 5% urea by pressurization, heating, or humidification by using a microwave oven, autoclave, electric pot, constant-temperature bath, or scalder.

(4) The activation method by using an EDTA solution of pH 8.0 and concentration 0.01 mol. by pressurization, heating, or humidification by using a microwave oven, autoclave, electric pot, constant-temperature bath, or scalder.

Those are main techniques currently employed.

Further, reference documents are listed below;

1) Shi S. R., Key, M. E., "Kalra, K. L; Antigen retrieval in formalin-fixed, paraffin-embedded tissues: an enhancement method for immunohistochemical staining based on microwave oven heating of tissue sections. J. Histochem. 39: 741–748,1991

2) Shi S. R., Cote R. J., Young L., Imam S. A. Taylor C. R.: Use of pH 9.5 Tris-HCl buffer containing 5% urea for antigen retrieval immunohistochemistry, Biotechnic & Histochemistry 71(4): 190–6, 1996 July.

3) Cattoretti G., Becker M. H. G, Key G., et al.: Monoclonal antibodies produced against recombinant parts of the Ki-67 molecule (MIB-1 to -3) stain proliferating cells in formalin fixed, paraffin-embedded, microwave processed tissues. Histochem J. 234: 611, 1992 (Abstr.)

4) Shin R. W., Iwaki T., Kitamono T., et al.: Hydrated autoclave pretreatment enhances tan immunoreactivity in formalin-fixed normal and Alzheimer's disease brain tissues. Lab. Invest. 64: 693–702, 1991

5) HAMAKAWA Shinji : An investigation on antigen activation by heat treatment during enzyme-antibody staining using anti-CD4 monoclonal antibody (Byohri to Rinshoh (Pathology and Clinical Pathology)) 1999, 17(11): 1201–1205)

6) HAMAKAWA Shinji : An investigation on an antigen activator in place of EDTA solution (Byohri Gijutu (Pathological Techniques)) 1999, 60: 10–14

Currently, the antigen activators are selected, depending upon object antigens. However, the current technique has disadvantages that the working procedures are complex, the activation of the antigen is imperfect, and the reproducibility of activation is poor.

SUMMARY OF THE INVENTION

An object of the present invention is to provide an activation method and reagent for unmasking an antigen during immuno-tissue-chemical staining.

The present invention directed to an optimum concentration solution of citraconic acid anhydride (systematic name: CCA) or 2-methylmaleic acid anhydride (common name: methylmaleic acid anhydride) which is most effective for the unmasking is based on a discovery that CCA is effective for unmasking antigens, when immuno-cells or immuno-tissues are stained chemically.

CCA of the present invention executes the unmasking of all of the target antigens with effect equivalent to or greater than the conventional activator.

Concretely, the unmasking method of the present invention is to unmask the tissue cells of which antigenicity of the antigen is masked by aldehyde during the immuno-tissue-cell-chemical staining.

The unmasking method of the present invention comprises the steps of soaking a slice of tissue cells stuck on a slide glass in CCA solution; heating for a sufficient time period the slice of tissue cells by either one of an electric pot, autoclave, microwave oven, scalder, or constant-temperature bath (including pressurization when the autoclave is used); and soaking the tissue cells in a buffer solution, after completing heating; and executing the enzyme-antibody staining.

Here, the CCA solution may be of concentration greater than or equal to 0.0001% and smaller than 100% and pH 1.0 to 12.0.

Further, 4 to 20% NaOH (sodium hydrate) aqueous solution may be added in the CCA solution in order to control the pH.

According to the present invention, the antigen-antibody reaction becomes more active, thereby reducing the antibody concentration and therefore antibody quantity, because the activator of the present invention activates the antigen more strongly than the conventional activator, and stabilizes the unmasked antigen. Therefore, reagent quantity is reduced. Further, diagnosis cost is reduced, because the activated antigen is stabilized, thereby raising diagnosis reproducibility and reducing false diagnosis.

PREFERRED EMBODIMENT OF THE INVENTION

Figure 1:
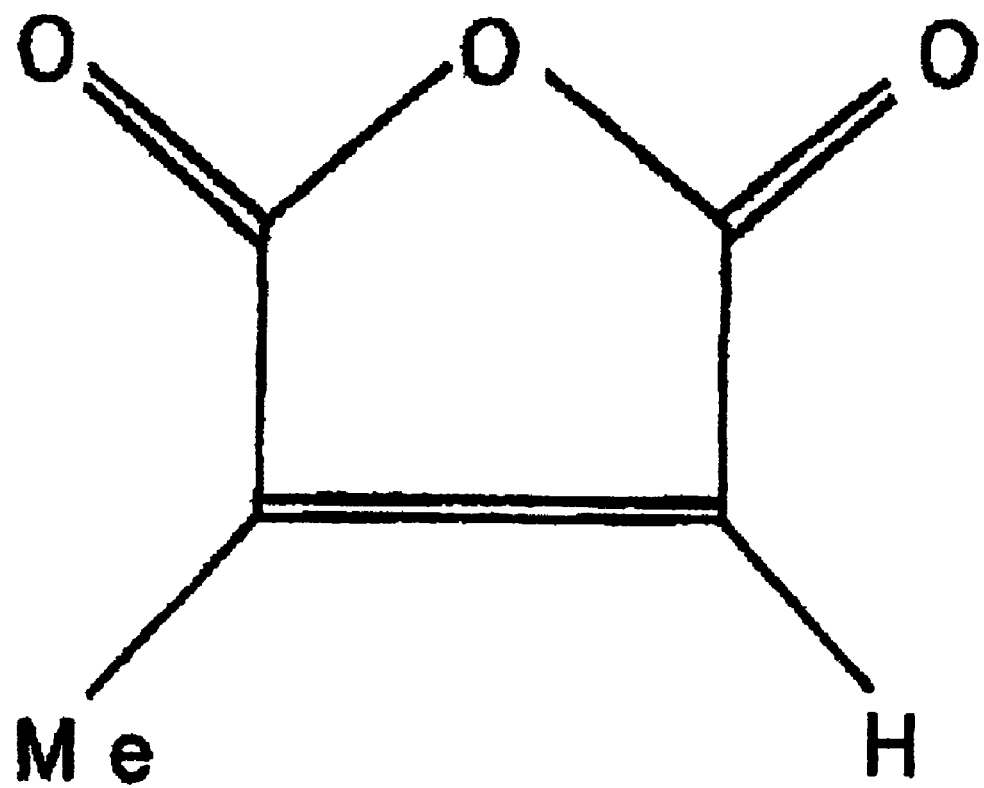
FIG. 1 is a chemical structure of citraconic add anhydride (CCA), where Me is methyl.

The present invention is useful in general in chemical staining of immuno-tissue-cells. The present invention provides an improved step for activating and unmasking the antigenicity inside the tissue cells which is masked by aldehyde fixation, thereby facilitating the antigen-antibody reaction. The above-mentioned improved step precedes the chemical staining.

The water which dissolves CCA as shown in FIG. 1 should not contain any impurity and any element which may cause any residue on the slide glass. Therefore, the water may preferably be distilled water, or more preferably be deionized water. The above-mentioned water is useful to obtain a impurity-free aqueous solution for an application to the chemical staining of the immuno-tissue-cells. The CCA concentration in the impurity-free aqueous solution may be greater than or equal to 0.001% and smaller than 100%, preferably be 0.001 to 10%, more preferably be 0.01 to 1%, and most preferably be 0.05%.

The pH of the CCA impurity-free aqueous solution may be acidic, neutral, or alkaline pH, for example, pH 1.0 to pH 12, preferably be pH 5.0 to pH 10.0, more preferably be pH 7.0 to pH 8.0, and most preferably be pH 7.4.

More specifically, The CCA solution may be of greater than or equal to 0.001% and smaller than 100% and pH 1.0 to pH 12, preferably be of 0.001 to 10% and pH 5.0 to pH 10.0, more preferably be of 0.01 to 1% and pH 7.0 to pH 8.0 pH, and most preferably be of 0.05% and pH 7.4.

The pH 7.4 is approximately the pH of living matters which is neither acidic nor alkaline, and therefore, most preferable for preventing damages against the tissue cells. The salt for controlling the pH may be NaOH in a form of 20 to 4% NaOH (sodium hydrate) aqueous solution, most preferably. The NaOH concentration should not deviate from above-mentioned range. For a preliminary treatment before the chemical staining, the activation is executed to the slice of the tissue cells which are buried in paraffin and fixed by aldehyde. Tissue cell treatment for recognizing antigens is called unmasking of antigen or simply "unmasking". The antigens to be unmasked are decided experimentally and are being reported in various documents. The CCA solution is applied, before the first antibody reaction, and preferably, immediately after the endogenous peroxidase treatment.

The slice of tissue cells is treated as follows.

The time period for treatment reaction may be long enough to break the bridges by aldehyde, as long as the tissue cells and antigens are not destroyed. The above-mentioned time period depends upon temperature, CCA concentration, thickness of tissue and time period for the aldehyde fixation. The suitable time period for the treatment reaction is easily decided as follows.

When the electric pot which is sold on the market is employed, 45 to 60 minute heating at 80 to 100° C., or preferably 45 minute heating at 100° C. is suitable.

Further, when the autoclave is employed, 15 to 20 minute pressurization and heating at 121° C., or preferably 20 minute pressurization and heating at 121° C. is suitable.

Further, when the microwave oven is employed, 15 to 20 minute heating at 98 to 100° C., or preferably 20 minute heating at 100° C. is suitable.

Further, when the gas range scalder is employed, 30 to 45 minute heating at 95 to 100° C., or preferably 45 minute heating at 100° C. is suitable.

Further, when the constant-temperature bath is employed, 16 hour minute (overnight) heating at 60 to 70° C., or preferably overnight heating at 60° C. is suitable.

In the present invention, CCA functions as a reagent for saving the tissues and cells damaged during the fixation by aldehyde such as formalin. The aldehyde fixation causes bridge bonds which mask the antigens in the tissue cells, thereby preventing the antigen from recognizing the antibody. As a result, the immuno-staining between the antigen and antibody is prevented, thereby leading a false negative decision and therefore a false evaluation of tisuue cel specimen. Here, the reagent CCA can destroy the bridge bondings by aldehyde and modifies the amino acids of the tissue cells. As a result, the amino acids which are reacting groups of the antigens which react against the antibodies are exposed to the reagent. However, it should be noted that non-specific stainings may often cause misunderstandings and erroneous diagnoses.

EXAMPLE

1) An organ tissue block such as a lymph node of fixed human or various animals, of 1 to 2 cm thickness is sliced out.

2) The sliced tissue block is fixed in an aldehyde fixation solution such as a 20% formalin solution/buffer solution, in the well-known manner, where the buffer solution is a 0.1 mol. and pH 7.4 phosphate buffer.

3) The fixed tissue block is dehydrated by alcohol, in the well-known manner.

4) The dehydrated tissue block is made dear by xylene, in the well-known manner.

5) The dear tissue block is soaked and wrapped in paraffin liquid melted by heating, in the well-known manner.

6) The paraffin wrapped tissue block is cooled and solidified, in the well-known manner.

7) The solidified tissue block is sliced as thin as 2 to 5 $\mu$m by a microtome and is stuck on a slide glass with exfoliation preventer, in the well-known manner.

8) The sliced tissue block wrapped in paraffin is deparaffinated by zylene, thereby exposing the tissue, and is water-washed through alcohol.

9) The slide glass with the specimen is soaked in CCA solution of 0.05% and pH 7.4 in order to have an affinity for the CCA solution. For example, when the specimen is the CD4 antigen, the slide glass with the slice in a basket is powerfully boiled in the electric pot filled with the CCA solution. The electric pot may be that sold on the market. Other antigens are activated similarly.

When the slice may be easily exfoliated, or it mat not be heat-resistive at a high temperature, it may be heated overnight (16 hours) at 60° C. in the constant temperature bath.

10) After completing the heat treatment, the slide glass with the tissue slice is picked out from the heating tool and is soaked in a buffer, where the buffer is tris buffer saline (1 liter—(0.05 mol. and pH 7.6 tris-HCl buffer) added with 8.5 g NaCl).

11) The tissue slice is stained by the enzyme-antibody staining method, in the well-known manner.

What is claimed is:

1. An antigen activation method for unmasking said antigen masked by aldehyde fixation which comprises the steps of:

soaking a slice of tissue cells stuck on a slide glass in citraconic acid anhydride (CCA) aqueous solution;

heating and destroying aldehyde bridges in said slice of tissue cells;

soaking said slice of tissue cells in a buffer solution, after completing heating; and executing an enzyme-antibody staining.

2. The antigen activation method according to claim 1, wherein said CCA aqueous solution is of concentration greater than or equal to 0.0001% and smaller than 100% and of pH 1.0 to 12.0.

3. The antigen activation method according to claim 1, wherein said CCA aqueous solution is of 0.001 to 10% and of pH 5.0 to pH 10.0.

4. The antigen activation method according to claim 1, wherein said CCA aqueous solution is of 0.01 to 1% and pH 7.0 to 8.0 pH.

5. The antigen activation method according to claim 1, wherein said CCA aqueous solution is of 0.05% and pH 7.4.

6. The antigen activation method according to claim 1, wherein said CCA aqueous solution is a solution of CCA dissolved in distilled water or deionized water.

7. The antigen activation method according to claim 1, wherein either one of an electric pot, autoclave, microwave oven, scalder, or constant-temperature bath is employed for said heating.

8. The antigen activation method according to claim 1, wherein 4 to 20% NaOH aqueous solution is added in said CCA aqueous solution.

9. The antigen activation method according to claim 1, wherein said slice of tissue cells stuck on a side glass is soaked in said CCA aqueous solution, before the first antibody reaction, and immediately after an endogenous peroxidase treatment.

\* \* \* \* \*

UNITED STATES PATENT AND TRADEMARK OFFICE
CERTIFICATE OF CORRECTION

PATENT NO.        : 6,960,450 B2                                         Page 1 of 1
APPLICATION NO. : 10/092462
DATED             : November 1, 2005
INVENTOR(S)       : Shigeki Namimatsu It is certified that error appears in the above-identified patent and that said Letters Patent is hereby corrected as shown below:

Cover page, Item (76) the inventor's address, "Shinjuku-cho" should read  -- Arajuku-machi --.

Signed and Sealed this

Fourteenth Day of September, 2010

David J. Kappos
*Director of the United States Patent and Trademark Office*